(12) United States Patent
Beilfuss et al.

(10) Patent No.: US 8,329,063 B2
(45) Date of Patent: *Dec. 11, 2012

(54) LOW-EMISSION FORMALDEHYDE DONOR PREPARATIONS

(75) Inventors: Wolfgang Beilfuss, Hamburg (DE); Ralf Gradtke, Tornesch (DE); Klaus Weber, Hamburg (DE)

(73) Assignee: Air Liquide Sante (International), Paris (FR)

( * ) Notice: Subject to any disclaimer, the term of this patent is extended or adjusted under 35 U.S.C. 154(b) by 1588 days.

This patent is subject to a terminal disclaimer.

(21) Appl. No.: 11/088,428

(22) Filed: Mar. 24, 2005

(65) Prior Publication Data

US 2005/0218379 A1 Oct. 6, 2005

(30) Foreign Application Priority Data

Mar. 24, 2004 (DE) .......................... 10 2004 014 447

(51) Int. Cl.
*C09K 3/00* (2006.01)

(52) U.S. Cl. .......................... 252/380; 252/384; 252/184

(58) Field of Classification Search ................... 252/380
See application file for complete search history.

(56) References Cited

U.S. PATENT DOCUMENTS

| 3,947,589 | A | * | 3/1976 | Misato et al. | 514/563 |
| 4,108,859 | A | * | 8/1978 | Tong | 546/289 |
| 4,655,815 | A | | 4/1987 | Jakubowski | |
| 4,761,184 | A | * | 8/1988 | Markessini | 106/217.6 |
| 4,844,891 | A | * | 7/1989 | Rosen et al. | 424/76.4 |
| 5,108,798 | A | * | 4/1992 | Guerro et al. | 427/389.8 |
| 5,332,765 | A | | 7/1994 | Lorentzen et al. | |
| 5,428,050 | A | | 6/1995 | Merianos | |
| 5,496,842 | A | | 3/1996 | Merianos | |
| 5,670,160 | A | | 9/1997 | Eggensperger et al. | |
| 6,348,483 | B1 | | 2/2002 | Beilfuss et al. | |
| 6,355,679 | B1 | * | 3/2002 | Beilfuss et al. | 514/529 |
| 6,465,498 | B2 | * | 10/2002 | Beilfuss et al. | 514/374 |
| 6,469,060 | B2 | | 10/2002 | Beilfuss et al. | |
| 2001/0021711 | A1 | * | 9/2001 | Beilfuss et al. | 514/245 |
| 2004/0082473 | A1 | * | 4/2004 | Beilfuss et al. | 504/114 |
| 2004/0151742 | A1 | | 8/2004 | Beilfuss et al. | |

FOREIGN PATENT DOCUMENTS

| DE | 040 26 756 | 2/1992 |
| DE | 041 41 953 | 6/1993 |
| DE | 042 42 082 | 6/1994 |
| DE | 197 22 858 | 11/1998 |
| DE | 198 42 116 | 3/2000 |
| DE | 199 61 621 | 7/2001 |
| DE | 101 22 380 | 11/2002 |
| EP | 0 327 220 | 8/1989 |
| GB | 2 011 790 | 7/1979 |
| WO | WO 01 41570 | 6/2001 |

OTHER PUBLICATIONS

Lewis, Richard J., Sr. (2002). "Antioxidant" in Hawley's Condensed Chemical Dictionary (14th Edition). John Wiley & Sons. Online version available at: http://www.knovel.com/knovel2/Toc.jsp?BookID=704&VerticalID=0.*
Patent Abstracts of Japan, publication date Mar. 2, 1990, application date Aug. 29, 1988, application No. 0214548; & JP 02 062833.

* cited by examiner

*Primary Examiner* — Peter F Godenschwager
(74) *Attorney, Agent, or Firm* — Young & Thompson

(57) ABSTRACT

A method of use and a composition with reduced formaldehyde and amine emissions. The composition contains an N-formal, an emission reducing additive, and monoethylene glycol. The emission reducing additive may be urea, a urea derivative, an amino acid, guanidine, or a guanidine derivative.

23 Claims, No Drawings

LOW-EMISSION FORMALDEHYDE DONOR PREPARATIONS

This application claims the benefit of priority under 35 U.S.C. §119 (a) and (b) to German Application No. DE 10 2004 014 447.8, filed Mar. 24, 2004, the entire contents of which are incorporated herein by reference.

BACKGROUND

The present invention relates to an N-formal-containing preservative with reduced formaldehyde and amine emission, and to the use thereof.

Formaldehyde donor compounds, for example O-formals and N-formals, are used as biocides in a series of products and preparations for reducing microbial growth. A series of documents is known which describe the use of O-formals and N-formals.

DE 42 42 082 A1 discloses hydrolysable polymeric resins and binders for antifouling paints. As well as hydrolysable polymeric resin, the binder system can also comprise cobiocides, such as dichlorophenyl-dimethylurea or 2-methylthio-4-tert-butylamino-6-cyclopropylamino-s-triazine.

U.S. Pat. No. 4,655,815 A1 discloses a synergistic antimicrobial mixture of 2-bromo-2-bromomethylglutaronitrile and formaldehyde donor. Examples of formaldehyde donors are 2-[(hydroxymethyl)amino]-2-methylpropanol, 2-hydroxyethyl-2-nitro-1,3-propanediol, mixtures of 5-hydroxymethyl-1-aza-3,7-dioxabicyclo-(3.3.0)octane, 2-[(hydroxymethyl)amino]ethanol, 1-(3-chloroallyl)-3,5,7-triaza-1-azoniaadamantane chloride, N-(3-chloroallyl)heximinium chloride, hexamethylenetetramine(hexamine) halohydrocarbon quats and dimethyloldimethylhydantoin.

EP 0 327 220 B1 describes a synergistic combination of selected formaldehyde donor with iodopropargyl compound. The disclosed compositions comprise, as preferred iodopropargyl compound, iodopropynyl butylcarbamate (IPBC) and, as formaldehyde donors, nontoxic and odour-free compounds which are suitable for use in bodycare compositions. However, the formaldehyde donors disclosed are relatively expensive substances.

DE 41 41 953 A1 discloses microbicidal compositions which comprise, as active ingredients, a combination of at least one iodopropargyl derivative and benzyl alcohol mono (poly)hemiformal. Moreover, further compounds, e.g. formaldehyde or its donor substances or guanidine derivatives, can be added to the active ingredient combination.

U.S. Pat. No. 5,428,050 A1 and U.S. Pat. No. 5,496,842 A1 disclose a water-soluble preservative mixture which comprises powders of (a) one or more methylol compounds or equivalents thereof, and (b) iodopropynyl alcohol, its ester, carbamate or ether derivative. The patent specifications disclose the synergistic combination of (a) and (b). However, undesired formaldehyde emissions are not discussed.

DE 197 22 858 A1 relates to compositions based on iodopropynyl and formaldehyde donor compounds and use thereof as preservatives. Examples of formaldehyde donor compounds are N,N'-methylenebis(5-methyloxazolidine), 3,3'-methylenebis(tetrahydro-2H-1,3-oxazine) and 1-aza-5-ethyl-3,7-dioxabicyclo[3.3.0]-octane. The compositions comprise iodopropynyl butylcarbamate as preferred iodopropynyl compound. As the IPBC content increases, the formaldehyde emissions increase, thus the biocidal effectiveness of the compositions in the gas phase also increases with increasing IPBC content. In the compositions, an addition of certain glycols has a positive influence on the odour of the compositions and reduces the emission of relatively volatile substances such as, for example, formaldehyde. The use of compositions which comprise iodopropynyl compounds is thus precluded if particularly low formaldehyde emissions are desired, or in the case of use in environments which are incompatible with iodopropynyl compounds. Moreover, compositions comprising iodopropynyl compounds have a tendency toward undesired discolorations.

The preservative of DE 40 26 756 A1 comprises a mixture of (a) an organic acid, (b) a monophenyl glycol ether and (c) a guanidine derivative. Further optional biocides mentioned are imidazolidineurea and/or hydantoin derivatives.

DE 199 61 621 A1 relates to compositions which comprise at least one bactericidal N-formal, at least one fungicide and at least one stabilizer. Particularly preferred formals are triazinetriethanol and N,N'-methylenebis(5-methyloxazolidine).

DE 198 42 116 A1 discloses stable microbicidal compositions which comprise derivatives of methylenebisoxazolidine and 1H-benzimidazol-2-ylcarbamic acid. Moreover, further active ingredients may be present, for example dimethylolurea, bis(hydroxymethyl)-5,5-dimethylhydantoin, diazolidinylurea, sodium hydroxylmethylglycinate or diuron (1,1-dimethyl-3-(3,4-dichlorophenyl)urea. However, these substances are relatively expensive and/or toxic. Carbendazime (methyl 1H-benzimidazol-2-ylcarbamate) is regarded as undesired due to its toxic properties (cancerogenic, mutagenic, reproduction-toxic) and its classification as a toxic substance (from 0.1% use concentration), although it is difficult to replace due to its good microbicidal effect.

DE 101 22 380 A1 discloses an alcohol-free liquid concentrate based on carboxylic acid salts and stabilizer components. The stabilizer component may be a formaldehyde donor compound.

GB 2 011 790 A1 discloses an aqueous germicidal composition comprising 0.1 to 5 parts by weight of 2-methyl-3-oxo-5-chlorothiazoline-1,2, 16 to 28.5 parts by weight of dimethylolurea and 40 to 72 parts by weight of one or more adducts which are formed from 2 mol of formaldehyde and aliphatic glycol with 2 to 8 carbon atoms and/or monoalkyl ethers of such a glycol having 1 to 6 carbon atoms in the ether group.

The Patent Abstract of Japan 02062833A (application No. 63214548) describes how a compound having amino groups can be added to a formaldehyde donor present in a water-based phase in order to prevent the release of formaldehyde.

In addition, various technical products based on N/O-formal are known. Thus, for example, the reaction product of formaldehyde or paraformaldehyde and ethanolamine (Grotan® BK=N,N',N''-tris(hydroxyethyl)hexahydrotriazine) has been used successfully as a preservative in the cutting fluid sector. Grotan® BK is a colourless to slightly yellowish liquid with a characteristic odour. On the basis of legal provisions, it has become a requirement to label a preparation containing greater than or equal to 0.1% of hexahydrotriazine (labelling requirement from 0.1% of hexahydrotriazine as R 43). In practice, a labelling of such substances or preparations (e.g. cutting fluid emulsions) cannot be carried out. As alternatives, therefore, biocides are sought which do not lead to a corresponding labelling, but on the other hand are comparatively effective, cost-effective and are acceptable from organoleptic considerations. These biocides should not necessarily comprise a large amount of hexahydrotriazine, but at the same time can release a large amount of formaldehyde, based on the weight.

An alternative to Grotan® BK which is used is, inter alia, the 1:1 condensation product of paraformaldehyde and isopropanolamine (N,N,N''-tris(β-hydroxypropyl)hexahydrotriazine, Grotan® WS). Grotan® WS is, due to the lower content of formaldehyde, somewhat less effective than Grotan® BK, and is also more odour-intensive and significantly more expensive than Grotan® BK.

For many years, a condensation product of paraformaldehyde and isopropanolamine (weight ratio 3:2, Mar® 71 or Grotan® OX or GrotaMar® 71, N,N'-methylenebis(5-methyloxazolidine) has also been used. The commercial products are anhydrous or low-water, colourless to slightly yellowish liquids with a characteristic pungent odour reminiscent of amine and formaldehyde. The biocidal effectiveness is very good due to the comparatively high formaldehyde content. However, the odour is perceived as a disadvantage during use. In particular, the pungent odour reminiscent of formaldehyde and the formaldehyde emission have been criticized.

Although, as has been mentioned, it is known from DE 197 22 858 A1 that certain glycols have a positive influence on the odour of compositions which comprise formaldehyde donor compounds and can reduce the emission of relatively volatile substances such as formaldehyde, the addition of relatively large amounts of odour-modifying additive, however, reduces, in an undesired way, the active ingredient content, based on the total weight. At the same time, emissions of odour-modifying additive (solvent) automatically arise, these emissions are in turn undesired.

Preparations based on dimethyloldimethylhydantoin (DMDMH) or tetramethylolglycoluril are also known. Apart from the fact that DMDMH and tetramethylolglycoluril are relatively expensive, they are solids or aqueous preparations which are unsuitable for certain fields of application. For example, it is impractical if, in the preparation of a dilute cutting fluid, a solid additive has firstly to be dissolved. In addition, a water fraction often has an unfavourable effect on the (storage) stability of certain active ingredients. Aqueous preparations also often have inadequate low-temperature stability. Water automatically reduces a high formaldehyde content and has an unfavourable effect on the emission of volatile constituents.

SUMMARY

An object of the present invention was consequently to provide a formaldehyde donor preparation as preservative for cutting fluid preparation as preservative for cutting fluid concentrates and cutting fluid emulsions, technical emulsions or as biocidal additive for products (e.g. diesel fuel) or in processes (e.g. in the offshore sector, boring fluids). This preparation should
1. be able to be formulated in a cost-effective manner,
2. release comparatively small amounts of formaldehyde and amine into the gas phase,
3. be acceptable in terms of odour,
4. have a high content of formaldehyde which can be cleaved off, i.e. the preparation should not automatically have a high solvent and water content,
5. be storage-stable, even over a prolonged period,
6. be miscible with further known biocidal, antimicrobial active ingredients and functional additives or auxiliaries without incompatibilities arising,
7. be able to be formulated in various forms, i.e. as a solid, semisolid, pasty or liquid preparation, and
8. be able to be formulated on the basis of formaldehyde donor compounds on the market, so that no new approval proceedings are necessary.

According to the invention, it has now been found that this object is achieved by a preservative which comprises (a) at least one N-formal, (b) at least one emission-reducing additive which is chosen from urea, urea derivatives, amino acids, guanidine and guanidine derivatives, and (c) monoethylene glycol. Preferred embodiments are the subject-matter of the dependent claims.

The N-formals used according to the invention are, for example, a reaction product or condensation product of a mono- or polyhydric, amino-substituted $C_1$ to $C_{10}$-alkyl-, -aryl-, -aralkylalcohol and a formaldehyde-supplying compound. Examples of N-formals are N,N',N''-tris(hydroxyethyl)hexahydrotriazine, N,N',N''-tris(β-hydroxypropyl)hexahydrotriazine, N-methylolchloroacetamide, cis-isomer of 1-(3-chloroallyl)-3,5,7-triaza-1-azoniaadamantane chloride, 1-(3-chloroallyl)-3,5,7-triaza-1-azoniaadamantane chloride, 5-(polyoxymethylene)-1-aza-3,7-dioxabicyclo[3.3.0]octane, ({[1-methyl-2-(5-methyloxazolidin-3-yl)ethoxy]methoxy}methoxy)methanol, 4,4-dimethyloxazolidine, 7a-ethyldihydro-1H,3H,5H-oxazolo[3,4-c]oxazole, 2-(hydroxymethylamino)ethanol, 1-(hydroxymethylamino)propan-2-ol and N,N'-methylenebis(5-methyloxazolidine). According to the invention, particular preference is given to N,N'-methylenebis(5-methyloxazolidine).

DESCRIPTION OF PREFERRED EMBODIMENTS

The preservatives according to the invention can also comprise one or more O-formals which are reaction products of a mono- or polyhydric $C_1$- to $C_{10}$-alkyl-, -aryl-, -aralkylalcohol or a glycol or glycol ether and a formaldehyde-supplying compound. Examples of O-formals are (ethylenedioxy)dimethanol, benzyl alcohol hemiformal, propylene glycol hemiformal and butyl diglycol hemiformal.

Examples of emission-reducing additives are chosen from glycoluril, tetramethylolglycoluril, dimethylhydantoin, dimethyloldimethylhydantoin, dimethylolurea, tetramethylolurea, imidazolidinylurea and diazolidinylurea. A particularly preferred emission-reducing additive is urea.

A compound which is covered by the definition of an emission-reducing additive is per definitionem no N-formal for the purposes of the description of the present invention. The emission-reducing additive can thus itself be an N-formal (a formaldehyde donor compound) (such as tetramethylolurea) and thus reduce the necessary amount of N-formal, which is advantageous, for example, if the N-formal is a hexahydrotriazine.

The preservative according to the invention can also comprise (d) one or more odour-modifying additives, such as alcohols and glycol ethers, where phenoxyethanol, phenoxypropanols, benzyl alcohol, phenethyl alcohol, phenylpropanols, phenylbutanols and phenylpentanols are particularly suitable, particular preference being given to phenoxyethanol. A further preferred odour-modifying additive is majantol (phenylpentanol).

Moreover, the preservative (e) can comprise one or more biocides, for example boric esters, boric acid salts, lactic acid derivatives, pyridine derivatives, phenols and parabens.

Examples of further biocides which can be used according to the invention can also be found in the BPD (Biocidal Product Directive) list of active ingredients. The combination with these known biocides serves to extend the spectrum of activity and/or to achieve synergistic increases in activity. Particular preference is given to combinations with thiabendazol, 2-mercaptopyridine N-oxide derivatives, such as pyrion-Na, zinc pyrithione, phenols, such as o-phenylphenol, parabens, thiophene compounds, such as N-cyclohexylbenzothiophene-2-carboxamide S,S-dioxide, amines, such as 2-amino-2-methylpropanol, quaternary ammonium salts such as benzalkonium chloride, didecyldimethyl-ammonium chloride, Vantocil IB, aldehydes, such as glutardialdehyde and o-phthaldialdehyde, and also active oxygen compounds, such as tert-butyl hydroperoxide.

The preservative according to the invention can also comprise (f) one or more additives, for example solvents, solubility promoters, corrosion inhibitors, alkalinizing agents, dyes, perfume, viscosity-modifying agents, foam inhibitors, emulsifiers, and antioxidants, dispersants, complexing agents, wetting agents, cleaning components, surfactants, pigments, ethereal oils, lubricant additives, care additives, fillers and polymers. The antioxidants used are preferably gallic acid esters, phenol derivatives, L-ascorbic acid and salts and derivatives thereof and tocopherols and derivatives thereof.

A preferred embodiment of the invention relates to a preservative which comprises 60 to 99% by weight, more preferably 70 to 95% by weight, in particular 80 to 92% by weight or 84 to 88% by weight, such as, for example, 86% by weight, of N-formal, in each case based on the sum of components (a), (b) and (c). Accordingly, the total amount of components (b) and (c) is preferably 1 to 40% by weight, more preferably 5 to 30% by weight, in particular 8 to 20% by weight or 12 to 16% by weight, such as, for example, about 14% by weight, based on the total amount of components (a), (b) and (c). Preferred weight ratios of (b) to (c) are in the range from 1:10 to 10:1, more preferably in the range from 1:5 to 5:1, in particular in the range from 1:2 to 2:1, such as, for example, about 1:2, about 1:1 or about 2:1.

In another preferred embodiment, the preservative according to the invention consists of (a) N-formal, (b) emission-reducing additive, (c) monoethylene glycol and optionally (d) odour-reducing additive and possibly a small amount of water (up to 10% by weight of water, preferably up to 5% by weight).

A further preferred embodiment relates to a preservative which comprises
a) 70 to 95% by weight, preferably 80 to 92% by weight, more preferably 84 to 88% by weight, in particular about 86% by weight, of N,N'-methylenebis(5-methyloxazolidine),
b) 2.5 to 15% by weight, preferably 5 to 10% by weight, such as about 5 or about 10% by weight, of urea, and
c) 2.5 to 15% by weight, preferably 5 to 10% by weight, such as about 5 or about 10% by weight of monoethylene glycol,
for example a preservative which consists of these two components in said amounts.

It is possible to formulate the preservative according to the invention by mixing together components (a), (b) and (c) and optionally further constituents. A preferred preparation, however, takes place by adding components (b) and (c) dissolved water to component (a) and then optionally stripping off the water.

A further preferred preparation takes place by condensing the amine on which the N-formal is based (e.g. isopropanolamine) with paraformaldehyde (for example in the molar ratio 2:3) to give the N-formal (for example N,N'-methylenebis(5-methyloxazolidine)), adding components (b) and (c) dissolved in water to component (a) and then stripping off the water.

In preservatives according to the invention it is possible to dispense with
(i) iodopropynyl compounds, in particular iodopropynyl butylcarbamate,
(ii) derivatives of 1H-benzimidazol-2-ylcarbamic acid,
(iii) isothiazolones, in particular 5-chloro-2-methyl-4-isothiazolin-3-one,
(iv) carboxylic acids, in particular salts of benzoic acid, propionic acid, salicylic acid, sorbic acid, 4-hydroxybenzoic acid, dehydracetic acid and 10-undecylenic acid and said free acids, and/or
(v) hydrolysable, polymeric resin,
and accordingly, these compounds are preferably not present.

In addition, the invention relates to the use of a preservative according to the invention for preserving a technical product, such as a cutting fluid, propellant, surface coating, a dispersion or a water-based paint.

Moreover, the invention relates to the use of (b) urea, urea derivatives, amino acids, guanidine or guanidine derivatives for reducing the formaldehyde and/or the amine emission of a composition which comprises (a) N-formal and (c) monoethylene glycol.

In addition, the invention relates to the use of (c) monoethylene glycol for reducing the formaldehyde and/or the amine emission of a composition which comprises an (a) N-formal and (b) urea, urea derivatives, amino acids, guanidine and/or guanidine derivatives.

Moreover, the invention relates to the use of mixtures of (b) urea, urea derivatives, amino acids, guanidine and/or guanidine derivatives with (c) monoethylene glycol for reducing the formaldehyde and/or the amine emission of a composition which comprises (a) N-formal.

The preservatives according to the invention may be solid, semisolid, pasty or liquid, they are preferably liquid. In a further preferred embodiment, the preservatives have a low content of water, for example they comprise 10% by weight of water or less, preferably 5% by weight or less, in particular 1% by weight or less of water, particular preference being given to anhydrous preservatives.

The preservative according to the invention offers, inter alia, the following advantages:
it can be formulated in a cost-effective manner from standard commercial components,
it has a high formaldehyde content, but at the same time greatly reduces formaldehyde emissions (gas phase),
it can be formulated in diverse forms, for example in a mixture with further biocides,
it has good storage stability, the slight clouding or precipitates sometimes observed with pure liquid formals such as Grotan® OX do not arise in the case of the preservative according to the invention,
through the addition of the emission-reducing additive it is possible to reduce the nonvolatile and volatile nitrosamines which form in small amounts in certain applications (e.g. as preservatives in cutting fluid emulsions),
upon storage in plastic containers, no neck-in effect arises, resulting in a cost saving (the plastic containers can be reused more often).

N-Formals are used to prevent microbial deposits on filters and in tank plants as fuel additive, also in modern speciality fuels which represent an emulsion of diesel fuel in water. An addition of urea to N-formal (such as N,N'-methylenebis(5-methyloxazolidine)) does not only reduce the emission of formaldehyde or formaldehyde donor compounds, but also brings about a reduction in the NO emission upon combustion of the propellant equipped with the preservative according to the invention.

These and further advantages are also evident from the examples below. (In the examples all data are in parts by weight unless indicated otherwise).

EXAMPLES

Grotan® OX is N,N'-methylenebis(5-methyloxazolidine). Grotan® OF is Grotan® OX mixed with urea in a weight ratio of 96:4.

1. Method of Determining Formaldehyde in the Gas Phase

The determination of the formaldehyde content in the gas phase above various preservatives was carried out using Dräger tubes 0.2/a (No. 6733081) in accordance with the instructions for use from Dräger Safety AG & Co. KGaA (9$^{th}$ Edition, July 2001). For this purpose, about 100 g of the sample to be investigated were introduced into a 250 ml wide-necked beaker with a screw lid and left to stand, in the closed state, for at least 3 hours at room temperature. The measurement was read off after 2 strokes on the scale 0.5 to 5 ppm, n=10. The measurements were carried out under comparable external conditions. Although the measurement results do not indicate an absolutely exact value in ppm of formaldehyde (standard deviation ±20 to 30%), the method is highly suitable for differentiating the formaldehyde emissions of different samples.

2. Method of Determining Ammonia (Amine) in the Gas Phase

The determination of the amine content in the gas phase above various preservatives was carried out using Dräger tubes 2/a (No. 6733231) in accordance with the instructions for use from Dräger Safety AG & Co. KGaA (9$^{th}$ Edition, July 2001). For this purpose, about 100 g of the sample to be investigated were introduced into a 250 ml wide-necked beaker with a screw lid and left to stand, in the closed state, for at least 3 hours at room temperature. The measurement was read off after one stroke on the scale. The measurements were carried out under comparable external conditions. Although the measurement results do not indicate an absolutely exact value in ppm of amine as $NH_3$ (standard deviation ±10 to 15%), the method is highly suitable for differentiating the amine emissions of different samples.

3. Formaldehyde and Amine Emissions of Preservatives

In the gas phase of preservatives formulated as described below, using the methods described under 1. and 2., the following formaldehyde and amine concentrations were measured in the gas phase (Table 1):

Preservatives A, B and C were prepared by adding urea and monoethylene glycol dissolved in water to Grotan® OX and stripping off the water on a rotary evaporator (2 hours at 60° C. and 30 mbar). Preservative D (comparative) was prepared by adding monoethylene glycol to Grotan® OX.

TABLE 1

|  | A | B | C | D (comparison) | E (comparison) | F (comparison) |
|---|---|---|---|---|---|---|
| Grotan ® OX | 186.0 | 186.0 | 186.0 | 186.0 | X |  |
| Grotan ® OF |  |  |  |  |  | X |
| Monoethylene glycol | 15.5 | 20.7 | 10.3 | 15.5 |  |  |
| Urea | 15.0 | 10.0 | 20.0 |  |  |  |
| After 4 days (gas phase) |  |  |  |  |  |  |
| ppm of amine | 9 | 8 | 12 | 10 | 10 | 15 |
| ppm of HCHO | 0 | 0 | 0 | 0.5-1 | 3 | 0.5-1 |
| After 2 weeks (gas phase) |  |  |  |  |  |  |
| ppm of amine | 9 | 8 | 12 | 12 | 15 | 17 |
| ppm of HCHO | 0 | 0 | 0 | 2 | 3-5 | 0.5-1 |
| After 4 weeks (gas phase) |  |  |  |  |  |  |
| ppm of amine |  | 9 |  |  |  |  |
| ppm of HCHO |  | 0 |  |  |  |  |
| After 11 weeks (gas phase) |  |  |  |  |  |  |
| ppm of amine | 5 | 5 | 9 | 8 | 13 | 20 |
| ppm of HCHO | 0 | 0 | 0 | 0.7 | 0.7 | 0.3 |

Table 1 shows that the formaldehyde emission of an N-formal-containing preservative (Grotan® OX, Example E) can be improved by adding urea (Grotan® OF, Example F), although the amine content in the gas phase is still undesirably high. The amine emissions of N-formal-containing preservative (Grotan® OX, Example E) can be improved by adding monoethylene glycol (Example D), although the formaldehyde content in the gas phase is still undesirably high. Surprisingly, in the case of the preservatives according to the invention (Example A, B and C), no formaldehyde can be detected in the gas phase, and the amine emissions are low.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A composition with reduced formaldehyde and amine emission which may be used as a preservative, comprising:
    a) between about 70% to about 95%, by weight, of N,N'-methylenebis(5-methyloxazolidine);
    b) between about 2.5% to about 15%, by weight, of urea; and
    c) between about 2.5% to about 15%, by weight, of monoethylene glycol,
    wherein said composition comprises less than about 10%, by weight, of water.

2. The composition of claim 1, further comprising at least one O-formal.

3. The composition of claim 2, wherein said O-formal comprises at least one member selected from the group consisting of:
    a) (ethylenedioxy)dimethanol;
    b) benzyl alcohol hemiformal;
    c) propylene glycol hemiformal; and
    d) butyl diglycol hemiformal.

4. The composition of claim 1, further comprising at least one emission reducing additive selected from the group consisting of:
    a) glycoluril;
    b) tetramethylolglycoluril;
    c) dimethylhydantoin;
    d) dimethyloldimethylhydantoin;
    e) dimethylolurea;
    f) tetramethanolurea;
    g) imdazolidinylurea; and
    h) diazolidinylurea.

5. The composition of claim 1, further comprising at least one odor modifying additive, wherein said modifying additive comprises at least one member selected from the group consisting of:

a) alcohols; and
b) glycol ethers.

6. The composition of claim 5, wherein said odor modifying additive further comprises at least one member selected from the group consisting of:
  a) phenoxyethanol;
  b) phenoxypropanols;
  c) benzyl alcohol;
  d) phenethyl alcohol;
  e) phenylpropanols;
  f) phenylbutanols; and
  g) phenylpentanols.

7. The composition of claim 1, further comprising at least one biocide, wherein said biocide comprises at least one member selected from the group consisting of:
  a) boric esters;
  b) boric acid salts;
  c) lactic acid derivatives;
  d) pyridine derivatives;
  e) phenols; and
  f) parabens.

8. The composition of claim 1, further comprising at least one secondary additive, wherein said secondary additive comprises at least one member selected from the group consisting of:
  a) solvents;
  b) solubility promoters;
  c) corrosion inhibitors;
  d) alkalinizing agents;
  e) dyes;
  f) perfumes;
  g) viscosity modifying agents;
  h) foam inhibitors;
  i) emulsifiers; and
  j) antioxidants.

9. The composition of claim 8, wherein said antioxidant comprises at least one member selected from:
  a) gallic esters;
  b) phenol derivatives;
  c) L-ascorbic acid;
  d) L-ascorbic salts;
  e) L-ascorbic derivatives;
  f) tocopherols; and
  g) tocopherol derivatives.

10. The composition of claim 1, wherein the weight ratio of said emission reducing additive to said monoethylene glycol is between about 1:10 to about 10:1.

11. The composition of claim 10, wherein said ratio is between about 1:5 to about 5:1.

12. The composition of claim 11, wherein said ratio is between about 1:2 to about 2:1.

13. The composition of claim 1, wherein said composition comprises less than about 5%, by weight, of water.

14. The composition of claim 13, wherein said composition comprises less then 1%, by weight, of water.

15. The composition of claim 14, wherein said composition is an anhydrous composition.

16. A composition with reduced formaldehyde and amine emission, which may be used as a preservative comprising:
  a) between about 80% to about 92%, by weight, of N,N'-methylenebis(5methyloxazolidine);
  b) between about 5% to about 10%, by weight, of urea; and
  c) between about 5% to about 10%, by weight, of monoethylene glycol,
  wherein said composition comprises less than about 10%, by weight, of water.

17. A composition with reduced formaldehyde and amine emission, which maybe used as a preservative comprising:
  a) between about 84% to about 88%, by weight, of N,N'-methylenebis(5-methyloxazolidine);
  b) between about 5% to about 10%, by weight, of urea; and
  c) between about 5% to about 10%, by weight, of monoethylene glycol,
  wherein said composition comprises less than about 10%, by weight, of water.

18. The composition of claim 17, wherein said composition comprises about 86%, by weight, of said N,N'-methylenebis(5-methyloxazolidine).

19. A method which may be used for preserving products, said method comprising combining a composition with a product so as to preserve said product, wherein said composition comprises:
  a) at least one N-formal;
  b) at least one emission reducing additive, wherein said reducing additive comprises at least one member selected from the group consisting of:
    1) urea;
    2) urea derivatives;
    3) amino acids;
    4) guanidine; and
    5) guandine derivatives; and
  c) monoethylene glycol,
  and said composition comprises less than about 10%, by weight, of water.

20. The method of claim 19, wherein said product comprises at least one member selected from the group consisting of:
  a) a cutting fluid;
  b) a propellant;
  c) a surface coating;
  d) a dispersion; and
  e) a water based paint.

21. A method which may be used for reducing an emission of a composition, comprising:
  reducing an emission of a first composition by adding a second composition to said first composition, wherein:
  a) said emission comprises at least one member selected from the group consisting of:
    1) a formaldehyde emission; and
    2) an amine emission;
  b) said first composition comprises:
    1) at least one N-formal; and
    2) monoethylene glycol; and
  c) said second composition comprises at least one member selected from the group consisting of:
    1) urea;
    2) urea derivatives;
    3) amino acids;
    4) guanidine; and
    5) guanidine derivatives; and
  d) said first composition and said second composition, in combination, comprise less than about 10%, by weight, of water.

22. A method which may be used for reducing an emission of a composition, comprising:
  reducing an emission of a composition by adding monoethylene glycol to said composition, wherein:
  a) said emission comprises at least one member selected from the group consisting of:
    1) a formaldehyde emission; and
    2) an amine emission; and
  b) said composition comprises:
    1) at least one N-formal;

2) urea;
   3) urea derivatives;
   4) amino acid;
   5) guanidine; and
   6) guanidine derivatives,
   wherein said composition with said added monoethylene glycol comprises less than about 10%, by weight, of water.

23. A method which may be used for reducing an emission of a composition, comprising:
   reducing an emission of a composition by adding a mixture to said composition; and
   stripping off water from the composition with the added mixture, wherein:
   a) said emission comprises at least one member selected from the group consisting of:
      1) a formaldehyde emission; and
      2) an amine emission;
   b) said composition comprises at least one N-formal; and
   c) said mixture comprises:
      1) monoethylene glycol;
      2) urea;
      3) urea derivatives;
      4) amino acids;
      5) guanidine; and
      6) guanidine derivatives.

* * * * *